(12) United States Patent
Harada et al.

(10) Patent No.: US 6,680,389 B2
(45) Date of Patent: Jan. 20, 2004

(54) ESTER COMPOUNDS

(75) Inventors: Yuji Harada, Niigata-ken (JP); Jun Hatakeyama, Niigata-ken (JP); Yoshio Kawai, Niigata-ken (JP); Michitaka Ootani, Saitama-ken (JP); Satoru Miyazawa, Saitama-ken (JP); Kentaro Tsutsumi, Saitama-ken (JP); Kazuhiko Maeda, Tokyo (JP)

(73) Assignees: Sihn-Etsu Chemical Co., Ltd., Tokyo (JP); Central Glass Co., Ltd., Yamaguchi-ken (JP)

( * ) Notice: Subject to any disclaimer, the term of this patent is extended or adjusted under 35 U.S.C. 154(b) by 0 days.

(21) Appl. No.: 10/178,482

(22) Filed: Jun. 25, 2002

(65) Prior Publication Data

US 2002/0198390 A1 Dec. 26, 2002

(30) Foreign Application Priority Data

Jun. 25, 2001 (JP) .......................................... 2001-190610
Jun. 25, 2001 (JP) .......................................... 2001-190611
Nov. 28, 2001 (JP) .......................................... 2001-362599

(51) Int. Cl.$^7$ ................... C07D 307/56; C07D 307/77; C07D 333/50
(52) U.S. Cl. ........................... 549/313; 42/292; 42/298
(58) Field of Search ................................ 549/292, 313, 549/298, 42

(56) References Cited

U.S. PATENT DOCUMENTS

| 4,491,628 | A |   | 1/1985 | Ito et al. |
| 5,310,619 | A |   | 5/1994 | Crivello et al. |
| 6,207,342 | B1 | * | 3/2001 | Takechi et al. .......... 430/270.1 |

FOREIGN PATENT DOCUMENTS

| JP |   | 63-27829 |   | 2/1988 |
| JP |   | 2-27660 B2 |   | 6/1990 |
| JP |   | 09073173 A |   | 3/1997 |
| JP |   | 09230595 A |   | 9/1997 |
| JP |   | 10010739 A |   | 1/1998 |
| JP |   | 11-119434 | * | 4/1999 |
| WO |   | WO 97/33198 |   | 9/1997 |

OTHER PUBLICATIONS

Takechi, Satoshi, 'Chemically–amplified photoresist and its patterning forming pattern with good dry etching resistance' 130:318608 (1999).*

* cited by examiner

Primary Examiner—Amelia Owens
(74) Attorney, Agent, or Firm—Millen, White, Zelano & Branigan

(57) ABSTRACT

Acrylic esters containing fluorine at α-position and having a lactone ring introduced into the ester side chain thereof are novel. Polymers obtained from the acrylic esters have a high transparency to VUV and good adhesion to substrates and are used to formulate chemically amplified resist compositions for lithographic microfabrication.

16 Claims, No Drawings

ESTER COMPOUNDS

This invention relates to novel ester compounds which are useful as a monomer to produce base polymers for use in chemically amplified resist compositions for microfabrication.

BACKGROUND OF THE INVENTION

In the drive for higher integration and operating speeds in LSI devices, the pattern rule is made drastically finer. The rapid advance toward finer pattern rules is grounded on the development of a projection lens with an increased NA, a resist material with improved performance, and exposure light of a shorter wavelength. To the demand for a resist material with a higher resolution and sensitivity, acid-catalyzed chemical amplification positive working resist materials are effective as disclosed in U.S. Pat. No. 4,491,628 and U.S. Pat. No. 5,310,619 (JP-B 2-27660 and JP-A 63-27829). They now become predominant resist materials especially adapted for deep UV lithography. Also, the change-over from i-line (365 nm) to shorter wavelength KrF laser (248 nm) brought about a significant innovation. Resist materials adapted for KrF excimer lasers enjoyed early use on the 0.30 micron process, went through the 0.25 micron rule, and currently entered the mass production phase on the 0.18 micron rule. Engineers have started investigation on the 0.15 micron rule, with the trend toward a finer pattern rule being accelerated.

For ArF laser (193 nm), it is expected to enable miniaturization of the design rule to 0.13 μm or less. Since conventionally used novolac resins and polyvinylphenol resins have very strong absorption in proximity to 193 nm, they cannot be used as the base resin for resists. To ensure transparency and dry etching resistance, some engineers investigated acrylic and alicyclic (typically cycloolefin) resins as disclosed in JP-A 9-73173, JP-A 10-10739, JP-A 9-230595 and WO 97/33198.

With respect to $F_2$ excimer laser (157 nm) which is expected to enable further miniaturization to 0.10 μm or less, more difficulty arises in insuring transparency because it was found that acrylic resins which are used as the base resin for ArF are not transmissive to light at all and those cycloolefin resins having carbonyl bonds have strong absorption. It was also found that poly(vinyl phenol) which is used as the base resin for KrF has a window for absorption in proximity to 160 nm, so the transmittance is somewhat improved, but far below the practical level.

SUMMARY OF THE INVENTION

An object of the invention is to provide a novel ester compound useful as a monomer to produce a base polymer which has a high transmittance to vacuum ultraviolet radiation of up to 300 nm, especially $F_2$ (157 nm), $Kr_2$ (146 nm), KrAr (134 nm) and $Ar_2$ (121 nm) excimer laser beams, and is useful as the base resin in a chemically amplified resist composition.

It has been found that resins obtained from acrylic acid derivatives containing fluorine at α-position have a high transparency and that resins synthesized from the same monomer, but having a lactone ring introduced into the ester side chain thereof is outstandingly improved in adhesion to substrates.

The present invention provides an ester compound of the following general formula (1):

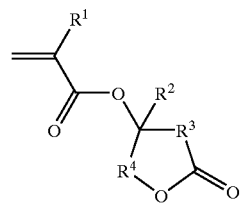

(1)

Herein $R^1$ is a fluorine atom or a straight, branched or cyclic alkyl group of 1 to 15 carbon atoms having at least one fluorine atom, $R^2$ is hydrogen, a fluorine atom or a straight, branched or cyclic alkyl or fluorinated alkyl group of 1 to 15 carbon atoms, $R^3$ and $R^4$ each are a single bond or an alkylene group of 1 to 20 carbon atoms.

The present invention also provides an ester compound of the following general formula (2):

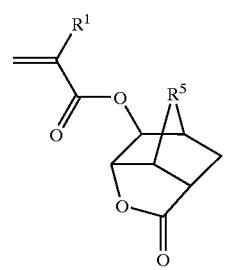

(2)

Herein $R^1$ is as defined above, and $R^5$ is an alkylene group of 1 to 10 carbon atoms, an oxygen atom or a sulfur atom.

Preferably, $R^1$ in formula (1) or (2) is trifluoromethyl.

DESCRIPTION OF THE PREFERRED EMBODIMENTS

Among the approaches for increasing the transmittance of resins in proximity to 157 nm, it is believed effective to reduce the number of carbonyl groups and carbon-to-carbon double bonds. It has been ascertained that the introduction of fluorine atoms into monomeric units makes a great contribution to the transmittance improvement. Specifically, the inventor has discovered that polymers obtained from acrylate monomers containing fluorine at α-position as represented by the structure of formulae (1) and (2) below have a high transparency in proximity to 157 nm. Since the acrylate monomers additionally have a lactone ring on the ester side chain, the polymers are drastically improved in adhesion to substrates.

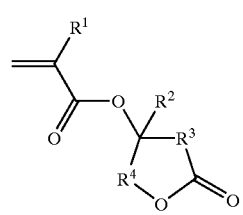

(1)

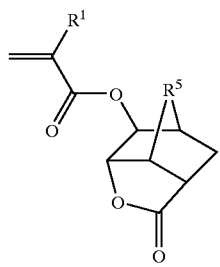

(2)

Herein $R^1$ is a fluorine atom or a straight, branched or cyclic alkyl group of 1 to 15 carbon atoms, especially 1 to 10 carbon atoms, having at least one fluorine atom. $R^2$ is hydrogen, a fluorine atom or a straight, branched or cyclic alkyl or fluorinated alkyl group of 1 to 15 carbon atoms, especially 1 to 10 carbon atoms. $R^3$ and $R^4$ each are a single bond or an alkylene group of 1 to 20 carbon atoms, especially 1 to 5 carbon atoms. $R^5$ is an alkylene group of 1 to 10 carbon atoms, an oxygen atom or a sulfur atom.

Specifically, suitable alkyl groups include, but are not limited to, methyl, ethyl, n-propyl, isopropyl, n-butyl, isobutyl, tert-butyl, pentyl, cyclopentyl, hexyl, cyclohexyl, octyl, decyl, and dodecyl. Suitable alkyl groups having a fluorine atom(s) and fluorinated alkyl groups include the foregoing alkyl groups in which some or all of the hydrogen atoms are substituted with fluorine atoms. Suitable alkylene groups correspond to the foregoing alkyl groups with one hydrogen atom being eliminated therefrom.

Preferably, $R^1$ in formula (1) or (2) is trifluoromethyl.

Illustrative examples of the ester compounds of the invention are given below, but the invention is not limited thereto.

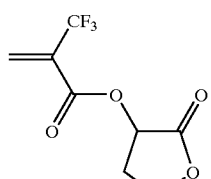

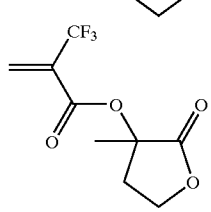

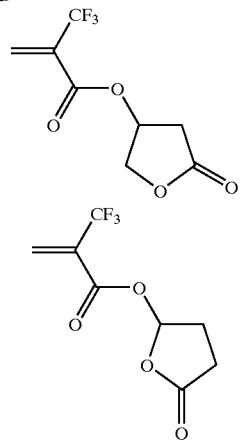

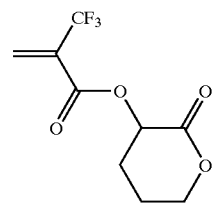

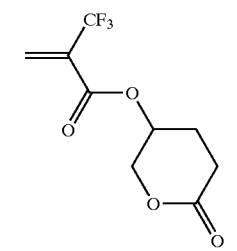

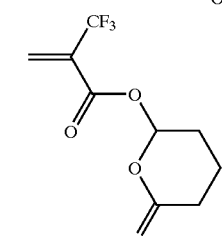

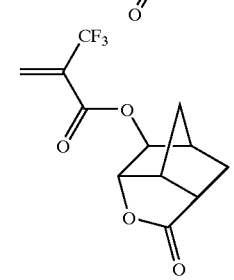

-continued

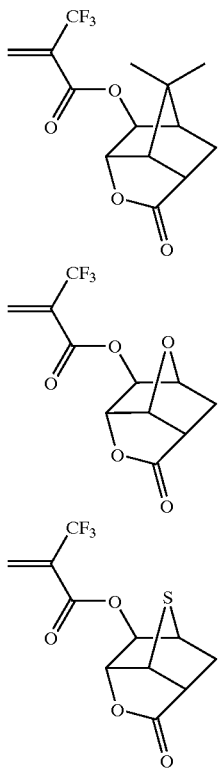

The ester compounds of the invention can be prepared, for example, by the following processes, but the invention is not limited thereto.

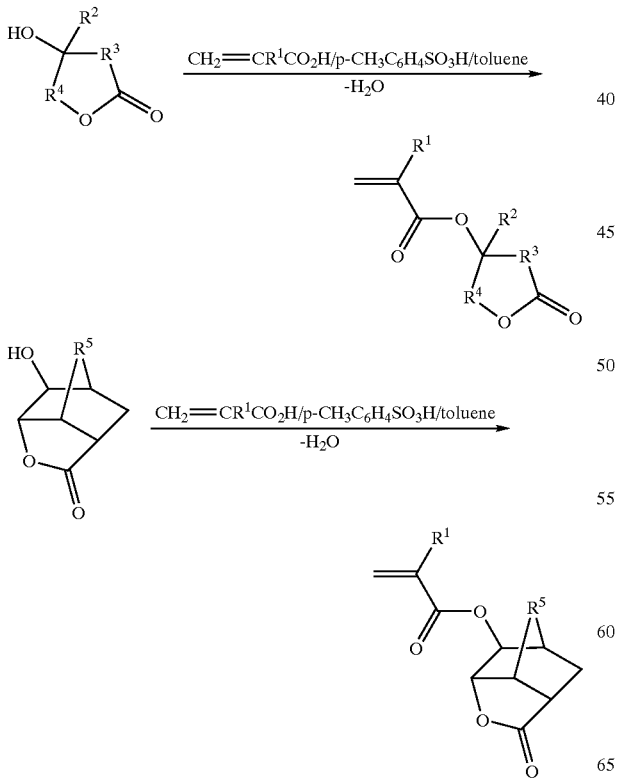

Herein, $R^1$ to $R^5$ are as defined above. The reactions readily proceed under well-known conditions. In one referred procedure, the reactant, that is, the alcohol having a lactone ring, an equimolar amount of an acrylic acid having fluorine at α-position, and a catalytic amount of an acid, typically toluenesulfonic acid are successively or simultaneously added to a solvent such as toluene. The system is heated under reflux for reaction. The water formed is removed from the system so that equilibrium is shifted toward the product side, thereby completing the reaction.

The ester compounds of the invention are useful as a monomer for the production of polymers. The polymers obtained therefrom are used as a base resin to formulate resist compositions which are improved in transparency and substrate adhesion and useful in micropatterning with electron beam and deep UV, especially $F_2$ excimer laser beam.

EXAMPLE

Examples of the invention are given below by way of illustration and not by way of limitation.

Synthesis Example 1
Synthesis of Monomer 1

In a flask, 33.0 g of α-hydroxy-γ-butyrolactone, 50.0 g of α-trifluoromethylacrylic acid, and 12.3 g of p-toluenesulfonic acid monohydrate were dissolved in 200 g of toluene along with a polymerization stabilizer. With a Dean-Stark trap attached to the flask, the mixture was heated under reflux for 4 hours for reaction to take place, while the water formed was removed. The reaction mixture was cooled to room temperature and worked up in a conventional manner. The oily substance thus obtained was purified by silica gel chromatography, collecting 60.1 g of Monomer 1 shown below. The yield was 83.0%.

Monomer 1

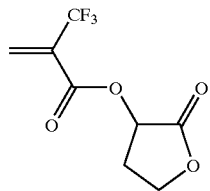

$^1$H-NMR (CDCl$_3$, 270 MHz): δ 2.38 (m, 1H), 2.78 (m, 1H), 4.31–4.52 (m, 2H), 5.57 (t, 1H), 6.56 (m, 1H), 6.83 (m, 1H) FT-IR (NaCl): 2997, 2927, 1786, 1743, 1401, 1377, 1244, 1222, 1176, 1144, 1107, 1016 cm$^{-1}$

Synthesis Example 2
Synthesis of Monomer 2

In a flask, 36.7 g of Alcohol 1 shown below, 50.0 g of α-trifluoromethylacrylic acid, and 9.1 g of p-toluenesulfonic acid monohydrate were dissolved in 200 g of toluene along with a polymerization stabilizer. With a Dean-Stark trap attached to the flask, the mixture was heated under reflux for 24 hours for reaction to take place, while the water formed was removed. The reaction mixture was cooled to room temperature and worked up in a conventional manner. The oily substance thus obtained was purified by silica gel chromatography, collecting 50.5 g of Monomer 2 shown below. The yield was 76.8%.

Alcohol 1

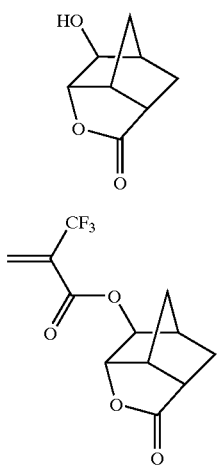

Monomer 2

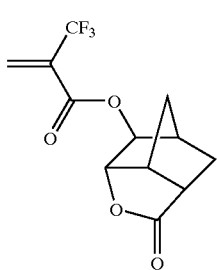

$^1$H-NMR (CDCl$_3$, 270 MHz): δ 1.69–1.80 (m, 2H), 1.98–2.08 (m, 2H), 2.50–2.61 (m, 2H), 3.24 (m, 1H), 4.59 (m, 1H), 4.73 (m, 1H), 6.46 (m, 1H), 6.75 (m, 1H) FT-IR (NaCl): 2981, 2887, 1786, 1738, 1452, 1408, 1383, 1358, 1246, 1178, 1144, 1115, 1095, 1014, 993 cm$^{-1}$

Synthesis Example 3

Synthesis of Monomer 3

As in Synthesis Example 2, Monomer 3 was synthesized from starting Alcohol 2. The yield was 72.1%.

Alcohol 2

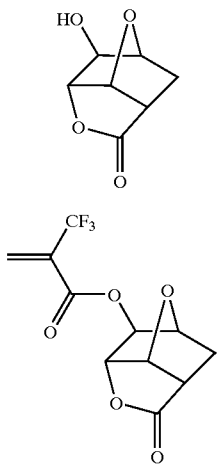

Monomer 3

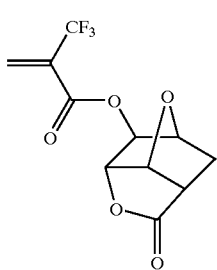

$^1$H-NMR (CDCl$_3$, 270 MHz): δ 1.62–1.79 (m, 2H), 1.93–2.03 (m, 2H), 2.52–2.71 (m, 2H), 3.33 (m, 1H), 4.45 (m, 1H), 4.78 (m, 1H), 6.41 (m, 1H), 6.71 (m, 1H) FT-IR (NaCl): 2980, 2885, 1782, 1734, 1452, 1408, 1383, 1352, 1244, 1170, 1141, 1113, 1095 cm$^{-1}$

Japanese Patent Application Nos. 2001-190610, 2001-190611 and 2001-362599 are incorporated herein by reference.

Reasonable modifications and variations are possible from the foregoing disclosure without departing from either the spirit or scope of the present invention as defined by the claims.

What is claimed is:

1. An ester compound of the following general formula (1):

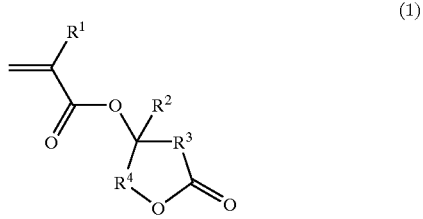

wherein $R^1$ is a straight, branched or cyclic alkyl group of 1 to 15 carbon atoms having at least one fluorine atom, $R^2$ is hydrogen, a fluorine atom or a straight, branched or cyclic alkyl or fluorinated alkyl group of 1 to 15 carbon atoms, $R^3$ and $R^4$ each are a single bond or an alkylene group of 1 to 20 carbon atoms.

2. An ester compound of the following general formula (2):

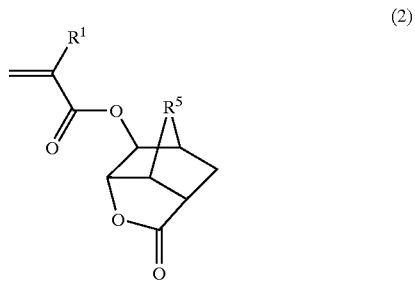

wherein $R^1$ is a fluorine atom or a straight, branched or cyclic alkyl group of 1 to 15 carbon atoms having at least one fluorine atom, and $R^5$ is an alkylene group of 1 to 10 carbon atoms, an oxygen atom or a sulfur atom.

3. An ester compound of claim 2, wherein $R^1$ in formula (2) is trifluoromethyl.

4. An ester compound of the formula (1):

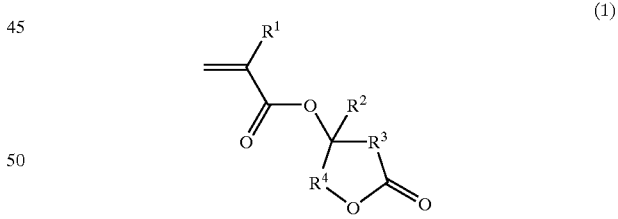

wherein $R^1$ is trifluoromethyl, $R^2$ is hydrogen, a fluorine atom or a straight, branched or cyclic alkyl or fluorinated alkyl group of 1 to 15 carbon atoms, $R^3$ and $R^4$ each are a single bond or an alkylene group of 1 to 20 carbon atoms.

5. A compound according to claim 1, wherein $R^1$ is a straight, branched or cyclic alkyl group of 1 to 10 carbon atoms having at least one fluorine atom.

6. A compound according to claim 1, wherein $R^2$ is methyl, ethyl, n-propyl, isopropyl, n-butyl, isobutyl, tert-butyl, pentyl, cyclopentyl, hexyl, cyclohexyl, octyl, decyl, or dodecyl, which in each case is optionally fluorinated.

7. A compound according to claim 1, wherein $R^1$ is methyl, ethyl, n-propyl, isopropyl, n-butyl, isobutyl, tert-butyl, pentyl, cyclopentyl, hexyl, cyclohexyl, octyl, decyl, or dodecyl, which in each case is fluorinated.

8. A compound according to claim 6, wherein R¹ is methyl, ethyl, n-propyl, isopropyl, n-butyl, isobutyl, tert-butyl, pentyl, cyclopentyl, hexyl, cyclohexyl, octyl, decyl, or dodecyl, which in each case is fluorinated.

9. A compound according to claim 1, wherein R³ is a single bond, methylene, ethylene or propylene and R⁴ is a single bond, methylene, ethylene or propylene.

10. A compound according to claim 8, wherein R³ is a single bond, methylene, ethylene or propylene and R⁴ is a single bond, methylene, ethylene or propylene.

11. A compound according to claim 2, wherein R¹ is a straight, branched or cyclic alkyl group of 1 to 10 carbon atoms having at least one fluorine atom.

12. A compound according to claim 2, wherein R¹ is methyl, ethyl, n-propyl, isopropyl, n-butyl, isobutyl, tert-butyl, pentyl, cyclopentyl, hexyl, cyclohexyl, octyl, decyl, or dodecyl, which in each case is fluorinated.

13. A compound according to claim 2, wherein R⁵ is methylene, —C(CH₃)₂-, —O— or —S—.

14. A compound according to claim 12, wherein R⁵ is methylene, —C(CH₃)₂-, —O— or —S—.

15. A compound according to claim 1, wherein said compound is selected from the following formulas:

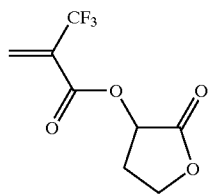

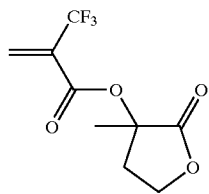

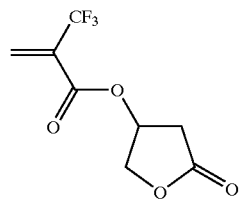

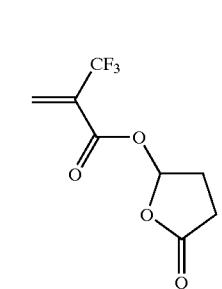

-continued

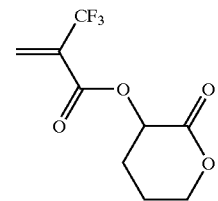

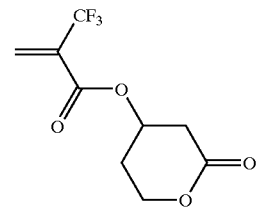

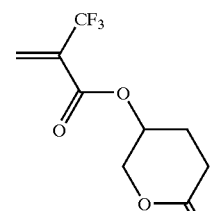

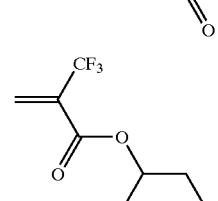

16. A compound according to claim 2, wherein said compound is selected from the following formulas:

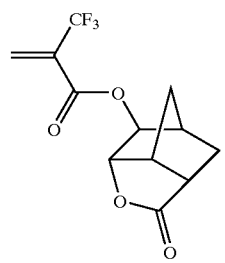

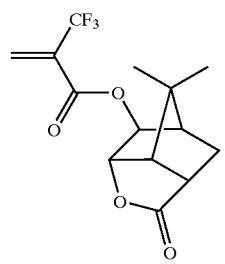

-continued
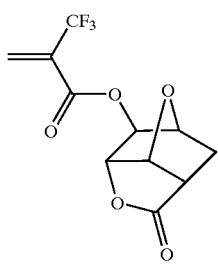
-continued
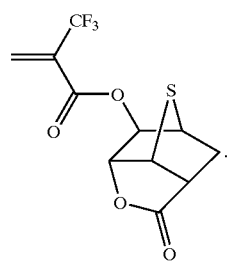
* * * * *